(12) United States Patent
Yarborough

(10) Patent No.: US 6,254,388 B1
(45) Date of Patent: *Jul. 3, 2001

(54) METHOD FOR WHITENING TEETH

(75) Inventor: David K. Yarborough, Sandy, UT (US)

(73) Assignee: BriteSmile, Inc., Walnut Creek, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/017,076

(22) Filed: Feb. 2, 1998

Related U.S. Application Data

(63) Continuation of application No. 08/708,527, filed on Sep. 5, 1996, now Pat. No. 5,713,738, which is a continuation-in-part of application No. 08/570,901, filed on Dec. 12, 1995, now Pat. No. 5,645,428.

(51) Int. Cl.$^7$ ..................................................... A61C 5/00
(52) U.S. Cl. ......................... 433/215; 424/616; 424/687; 424/688; 424/693; 424/709; 424/710; 424/717
(58) Field of Search ................................... 433/215, 216; 424/616, 687, 688, 693, 709, 710, 717

(56) References Cited

U.S. PATENT DOCUMENTS

| | | |
|---|---|---|
| 4,582,701 | 4/1986 | Piechota . |
| 4,661,070 | 4/1987 | Friedman . |
| 4,687,663 | 8/1987 | Schaeffer . |
| 4,877,401 | 10/1989 | Higuchi et al. . |
| 4,983,380 | 1/1991 | Yarborough . |
| 4,983,381 | 1/1991 | Torres Zaragoza . |
| 5,009,885 | 4/1991 | Yarborough . |
| 5,032,178 | 7/1991 | Cornell . |
| 5,041,280 | 8/1991 | Smigel . |
| 5,123,845 | 6/1992 | Vassiliadis et al. . |
| 5,306,143 | 4/1994 | Levy . |
| 5,318,562 | 6/1994 | Levy et al. . |
| 5,409,631 | 4/1995 | Fischer . |
| 5,645,428 * | 7/1997 | Yarborough ......................... 433/215 |
| 5,713,738 * | 2/1998 | Yarborough ......................... 433/215 |

FOREIGN PATENT DOCUMENTS

| | | |
|---|---|---|
| 8307091 | 10/1983 | (ES) . |
| 528007 | 9/1985 | (ES) . |

OTHER PUBLICATIONS

Journal of Endodontics, vol. 15, No. 3, Mar. 1989, Stewart Ho, DMD and Albert C. Goerig, DDS, MS, FICD An In Vitro Comparison of Different Bleaching Agents in the Discolored.

Asian Journal of Aesthetic Dentistry, vol. 1 No. 2 Jul. 1993, C.G. Toh "Clinical evaluation of a dual–activated bleaching system".

PR000001–PR000013, Patient records for an unnamed patient of an undisclosed dentist.

PR000014–PR000018, a dental laser made by HGM, Inc. with specification.

PR000019–PR000024, "The Argon Laser in Dentistry–A Review of Recent Articles".

PR000025–PR000031, Clinical Applications of the Spectrum Dental Laser (Draft Copy).

PR000032, Product Information for HGM, Inc. laser.

PR000033–PR000039, Westerman et al. "Argon Laser Irradiation in Root Surface Caries", *JADA*, Apr. 1994, pp. 401–7.

PR000040–PR000047, "Laser Parameters for the Argon Dental Laser".

PR000048–PR000051, "The Use of an Argon Laser for Polymerization of Composite Resin".

PR000052–PR000067, Dental Laser Information.

PRO000068–PR000075, Sparks, David E., "Argon Dental Laser".

PR000076–PR000077, Shofu Bleaching Composition Information.

PR000078–PR000083, Toh, C.G. "Clinical Evaluation of a Dual–activated Bleaching System," *Asian Journal of Aesthetic Dentistry*, 1993, pp. 65–70.

* cited by examiner

*Primary Examiner*—Nicholas D. Lucchesi
(74) *Attorney, Agent, or Firm*—Kalow & Springut LLP

(57) ABSTRACT

A method for whitening teeth which utilizes laser light to activate bleaching agents applied to the teeth. The mouth is first prepared so that the soft tissues of the gums are protected and only the teeth are exposed. The teeth are cleaned to remove any materials which will reduce or nullify the effects of the bleaching agents. A first bleaching composition comprising a peroxide compound is prepared and applied to the teeth. The teeth are exposed to laser light from an argon laser which light activates the peroxide to accelerate the bleaching process without heat. If further whitening is desired, a second bleaching composition comprising a peroxide compound is prepared and applied to the teeth. The teeth are briefly exposed to laser light from a carbon dioxide laser which heat activates the peroxide to accelerate the bleaching process.

29 Claims, No Drawings

METHOD FOR WHITENING TEETH

This application is a continuation of application Ser. No. 08/708,527, filed Sep. 5, 1996 now U.S. Pat. 5,713,738, which is a continuation-in-part of application Ser. No. 08/570,901, filed Dec. 12, 1995, now U.S. Pat. No. 5,645,428.

FIELD OF THE INVENTION

The present invention relates to a method for whitening teeth. More particularly, the present invention relates to a method for whitening teeth which utilizes laser light to activate bleaching agents.

BACKGROUND OF THE INVENTION

Development in the field of teeth whitening has led to the presently used method of "power bleaching," which is generally described as follows. A rubber sheet or dam is placed over the patient's teeth so that the teeth protrude through the sheet. The dam is made from latex rubber forced over each tooth and held in place with metal springs, clamps, and ligatures. This partially protects the soft tissues of the gums from the peroxides used in bleaching. However, since the rubber sheet stretches and does not custom fit the particular patient's mouth, the peroxide can leak around the rubber sheet and cause substantial discomfort to the patient. Typically, this method can be performed only on the upper or lower set of teeth at a time, not both.

Once the rubber sheet is in place, a peroxide solution is coated on the teeth. Since the bleaching effects of peroxide are slow, the common practice is to apply heat to the peroxide to accelerate the reaction. This is accomplished with the use of a heat lamp or heating iron. Although the heat accelerates the bleaching process, a substantial amount of time is still required so that the entire bleaching process must be performed over several appointments, resulting in inconvenience, time loss, and substantial expense.

The heat lamp activates the peroxide on a plurality of teeth simultaneously but, due to the amount of heat required where heat is the sole means for activating the peroxide, also exposes the patient's face to significant amounts of heat, which is quite uncomfortable and cannot be endured for a prolonged period. While the heating iron does not expose the patient's face to the same extent as the heat lamp, it takes a much longer time to perform the whitening since it affects only one or two teeth at a time. In addition, prolonged exposure to heat will increase the temperature of the pulp within the tooth, causing discomfort to the patient if the pulp temperature gets too high. Since the amount of heat commonly used in this type of procedure could kill the pulp and cause tooth loss if exposure is prolonged, continuous exposure must be limited. As a result, 2 to 5 office visits are required before adequate bleaching is attained.

Other prior art tooth bleaching techniques utilize both light and chemical activation of hydrogen peroxide to accelerate the bleaching process. For example, in Toh, C. G. "Clinical Evaluation of a Dual-activated Bleaching System," Asian Journal of Aesthetic Dentistry, Vol.1, No. 2, pp. 65–70 (July 1993), a powder containing potassium persulphinate (sold under the name "Oxone" by the DuPont Corp.) was mixed with solutions of hydrogen peroxide to form a paste. The paste was applied to discolored teeth and activated using a dental curing light. Two different concentrations of hydrogen peroxide were used—19% and 35%. A similar process is disclosed in U.S. Pat. No. 5,032,178, which also mentions the use of a 30–35i% aqueous solution of hydrogen peroxide, with Oxone as an accelerator, and a dental curing light.

The described use of the laser whitening method of the present invention has certain advantages over the use of dental curing lamps and the like. For example, heat lamps designed for tooth whitening, such as the Union Broach Illuminator, utilize halogen bulbs which are significant sources of yellow light. However, because the pulp tissue in living teeth is red, it rapidly absorbs the yellow light causing it to rise in temperature, resulting in patient discomfort. A similar problem arises with incandescent bulbs. Like halogen bulbs, they produce all wavelengths of visible light, much of which is absorbed by the tooth pulp.

Also known in the art is the use of a laser in combination with hydrogen peroxide to bleach teeth. For example, Spanish patent application no. ES 528007, in the name of Vicente M. Torres Zaragoza, generally discloses the use of laser radiation to accelerate the bleaching action of hydrogen peroxide, but does not disclose a specific type of laser or method of using a laser to accelerate bleaching. Unlike curing lights, lasers permit the practitioner to expose selected teeth to a focused beam of light, thereby concentrating the energy of the beam where it is needed.

From the foregoing it may be seen that there remains a need for a method of whitening teeth which better protects the soft tissues, shortens the time for the procedure, and reduces the discomfort to the patient.

In accordance with the principles of the present invention, the use of the light source of the described laser permits the practitioner to choose the specific wavelength of such light that will be most effective in eliminating the particular stain. It is advantageous to select a wavelength close to the color of the stain to be bleached so that the light will be absorbed primarily by the stain molecules rather than the tooth pulp.

SUMMARY OF THE PRESENT INVENTION

It is the object of the present invention to provide a method for whitening teeth that improves upon prior art methods and substantially reduces discomfort to the patient.

It is another object of the present invention to provide a method which can be performed within a short period of time, requiring only one office visit in most cases.

These and other objects of the present invention are accomplished through a method which utilizes laser light from an argon ion laser to activate bleaching agents applied to the teeth. The mouth is first prepared so that the soft tissues of the gums are protected and only the teeth are exposed. This is preferably accomplished using wax-like strips applied to the gums to isolate the gums from the chemical bleaching compounds. Typically, prior to a bleaching treatment, the teeth are cleaned to remove any materials which may reduce or nullify the effects of the bleaching agents. A mixture of peroxide is prepared and applied to the teeth. The teeth are then exposed to laser light from the argon laser to light activate the peroxide and accelerate the bleaching process.

In alternate embodiments of the invention, "boosters" and catalysts are used to further accelerate the bleaching process. Boosters are chemical compounds that, like hydrogen and carbamide peroxide, decompose into free oxygen radicals and thereby increase the effectiveness of the bleaching compound beyond that of the hydrogen peroxide alone by boosting the free oxygen radical concentration. A catalyst is any substance that causes a change in the rate of a chemical reaction without itself being consumed by the reaction.

In a preferred method of the present invention, a first bleaching step utilizing peroxide, light activated with an argon laser, is followed by a second bleaching step also utilizing peroxide, heat activated using a carbon dioxide laser.

These and other objects and advantages of the invention will become apparent from the following detailed description of the invention.

DETAILED DESCRIPTION OF THE INVENTION

In accordance with the present invention, whitening teeth can be achieved dramatically and quickly using laser energy to activate, i.e., accelerate the decomposition of, a peroxide solution applied to a patient's teeth. This method of whitening teeth can be performed in one office visit and subjects the patient to minimal discomfort.

Prior to applying a bleaching composition, it is necessary to isolate the patient's teeth so that only the teeth are exposed and the gums protected. This can be done using a rubber dam or sheet as described in prior art bleaching methods. Preferably, however, strips of a wax-like, moldable material having a pressure-sensitive adhesive quality are applied over the patient's upper and lower gums such that one side of each strip overlays the part of the teeth adjacent the gums. This side of each strip is molded so that it follows the contour of the gums adjacent the teeth, a process called "festooning." The strips are comprised of pectin, sodium carboxymethyl cellulose, gelatin, polyisobutylene, and silicone release paper. In a preferred embodiment, strips sold under the name Stomahesive® strips and manufactured by ConvaTec of Princeton, N.J., may be used. The strips are applied by removing the backing and slightly moistening the strip before application so that it adheres to the gums. These strips are chosen because they will not melt from the heat of a heat lamp or laser. Any remaining exposed soft tissues of the cheeks or gums are protected with tissue protectants that will break down peroxides, such as non-toxic metallic or enzymatic solutions created for this purpose, such as BriteSmile Laser Muco-Proe gel available from Ion Laser Technology, Inc. of Salt Lake City, Utah.

Typically, as a precursor to the bleaching process, and to maximize the bleaching effect of the peroxide and ensure complete coverage of the teeth, the front surfaces of the teeth are cleaned to remove any deposits that may interfere with the bleaching process, such as iron residues in lipstick, calculus, or plaque. However, this is not a required step in the process. A preferred cleaning solution contains: approximately 50% purified ethanol, although any concentration between 30% and 90% can be used; approximately 10% hydrogen peroxide, although any concentration between 0% and 30% can be used; an acid selected from the group consisting of phosphoric, citric, hydrochloric, acetic, and hydrofluoric acids; and deionized distilled water. Typically, the final concentration of acid is approximately 10%, although any concentration between 3% and 35% can be used. After cleaning, the teeth are rinsed with deionized distilled water so that no significant contaminants remain on the front surfaces of the teeth.

Following the cleaning step, the teeth are bleached according to any of the embodiments of the present invention disclosed herein. The use of lasers provides several benefits over heat lamps and the like. First, a laser may be chosen with a wavelength tailored to the color of the stain molecules so that the energy of the laser is largely absorbed by the stain molecules rather than the tooth pulp. Second, lasers provide much greater control over the density of the energy applied during the bleaching process by providing a narrow, focused beam of light.

In order to bleach teeth stained with brown and gray stain molecules, an argon ion laser is used to light activate the peroxide. Argon is chosen because in the visible spectrum it produces blue and green light with a wavelength in the range of 450–530 nanometers. Table 1 illustrates the relative power of the different wavelengths of light produced by a 500 mW argon ion laser.

TABLE 1

| Wavelength (nm) | Power (mW) | Spectrum |
| --- | --- | --- |
| 363.8 and below | 0.344 | Ultraviolet |
| 454.6 | 0.03 | Visible (blue) |
| 457.9 | 0.06 | Visible (blue) |
| 465.8 | 0.03 | Visible (blue) |
| 472.7 | 0.05 | Visible (blue) |
| 476.5 | 0.12 | Visible (blue) |
| 488 | 0.32 | Visible (blue) |
| 496.5 | 0.12 | Visible (blue) |
| 501.7 | 0.07 | Visible (geeen) |
| 514.5 | 0.40 | Visible (green) |
| 528.7 | 0.07 | Visible (green) |

As indicated in the table, in addition to the ultraviolet component, the argon laser generates two power spikes, one at 488 nm (blue) and one at 514.5 (green). Brown and gray stains absorb blue and green light well, but blood—the primary absorbing pigment in tooth pulp—does not. This is because both hemoglobin and oxyhemoglobin have relatively low energy absorption characteristics for light with wavelengths of 488 and 514.5 nm. In addition, unstained tooth enamel is white, which reflects most energy, particularly in the visible spectrum. Therefore, the light energy of the laser is absorbed primarily by the oxidizing molecules and not the tooth pulp. This has the advantage of both accelerating the bleaching process by concentrating the light energy where it is needed and minimizing patient discomfort by not significantly raising the temperature of the tooth pulp. The free oxygen radicals that result from the decomposition of, e.g., hydrogen peroxide into water, chemically react with and dechromatize the stain molecules.

In order to avoid overheating the tooth pulp of vital teeth (i.e., raising the pulp temperature more than 6° C.), the maximum energy applied to a tooth with an argon laser should not exceed 25 joules per application. In a preferred embodiment of the present invention, the total energy delivered to each tooth by the argon laser during laser bleaching is approximately 24 joules. This is achieved, for example, by the use of an argon laser with an output power of 800 mW for 30 seconds per tooth. Higher or lower power lasers may be used, with the exposure time per tooth adjusted accordingly. As a practical matter, the use of an argon laser with a power output less than 250 mW may not be feasible due to the length of exposure time required per tooth. In addition, the laser may be operated in pulsed mode or continuous wave. In a preferred embodiment, an argon laser with a 7.6 mm spot diameter is used, although smaller or larger beam diameters may also be used. Once all teeth have been treated, remaining bleaching mixture is removed from the teeth. If needed, the previous steps of applying the bleaching mixture and activating with the argon laser can be repeated.

The bleaching mixture may also include a booster to increase the free oxygen radical concentration and thus accelerate the chemical dechromatization reaction. A preferred bleaching mixture for use with an argon laser contains an oxygen radical generating agent such as a peroxide, a booster, a desensitizing and color stabilizing agent, a thickening agent, and a buffer for maintaining a desired pH range.

A preferred peroxide is hydrogen peroxide, although any peroxide may be selected from the group consisting of hydrogen peroxide, carbamide peroxide, calcium carbonate peroxide, sodium carbonate peroxide, and other oxygen radical generating agents. A liquid solution of hydrogen peroxide is used in the bleaching mixture. A preferred concentration of hydrogen peroxide in solution for use in the mixture is 35–50%, although any concentration between 3% and 50% can be used. The higher the concentration of peroxide, the greater the bleaching effect. The booster is preferably selected from the group consisting of ammonium persulfate, sodium persulfate, and potassium persulfate and has a final concentration in the mixture of 30%, although concentrations between 1% and 80% are effective. These compounds are used because they are particularly sensitive to light, i.e., they decompose at an accelerated rate when exposed to light from an argon laser, releasing free oxygen radicals in the process.

The desensitizing and color stabilizing agent is selected from the group consisting of fluoride, calcium, and phosphate, and is used at a final concentration in the mixture of 1% for fluoride, 5% for calcium, or 2% for phosphorus, although a concentration between 0.1% and 10% can be used for any of these substances. The thickening agent is selected from the group consisting of silicates, hydroxyethylceliulose, lanolate, palnitate, oleate, sodium lauryl sulfate, sodium stearate, calcium stearate, and other fatty acids. The use of sodium silicate has been found beneficial because it has an affinity for iron and other heavy metals, and thus helps to prevent them from breaking down the peroxide into molecular oxygen, which does not provide nearly the same bleaching effect as the desired free oxygen radicals. Typically, the thickening agents are used at a final concentration of 5%, although any concentration between 1% and 20% can be used. The buffer is selected from the group consisting of urea, sodium carbonate, sodium bicarbonate, calcium carbonate, calcium bicarbonate, ammonium hydroxide, and calcium hydroxide, although any buffering agent can be used. The concentration of the buffer will depend on what is necessary to maintain a pH between 7 and 11 because the peroxide decomposes more rapidly the higher the pH, although the optimal pH is between 7.8 and 9. Once mixed, a 1 to 2 millimeter layer of the bleaching mixture is applied to the front surface of the patient's teeth.

In order to further accelerate the bleaching process, additional steps may be employed. First, in order to thermally agitate and increase diffusion of the peroxide, an infrared heat lamp may be used in conjunction with the laser. Although, for the reasons discussed above, such a lamp is not preferred as the primary means of activation of the peroxide, it is useful as an adjunct to the argon laser to maintain the teeth at a slightly elevated temperature (100–104° F.) to effect the diffusion of the peroxide into the teeth.

Second, a pigment may be added to the bleaching composition to further increase the amount of light energy absorbed by the oxidizing molecules. For example, if a yellow pigment is added to the composition, it will absorb the blue and green light from an argon laser but substantially reflect yellow light generated by the infrared lamp. Because the pulp in live teeth is red, yellow light is absorbed by the pulp, causing pain and inflammation if the pulp gets too hot. Thus, the use of a yellow pigment also acts to prevent harm to the teeth by helping to lower the pulp temperature during bleaching. In a preferred embodiment, FD&C yellow 5 LAKE or 6 LAKE is used as the pigment. Similarly, a red or orange pigment may be used in conjunction with the argon laser. The red or orange pigment will also help the bleaching mixture absorb blue, green and yellow light, and reflect any red or orange light.

As an additional step to enhance the effectiveness of the process, the teeth may be subjected to a preconditioning step prior to the laser activated bleaching step, as follows. An additional coat of bleaching mixture, as described above, is applied to the teeth and allowed to remain in the teeth for a period sufficient to permit the mixture to soak into the teeth. This step helps to clean the teeth and soak them with peroxide in advance of the argon laser bleaching step. Typically, a period of about 30 minutes is adequate, although a period between 15 and 60 minutes may be used. This mixture is removed and a fresh mixture placed on the teeth for the laser activation step described above. It has been found that this preconditioning step improves the whitening effect of the subsequent laser activated bleaching step.

The use of an argon laser in conjunction with a peroxide bleaching composition may be sufficient to achieve the desired shade of whiteness in many patients in a single office visit. However, while an argon laser is effective for whitening teeth with brown and gray stains because of the blue light generated, its effectiveness decreases as the teeth become whiter. This is because as the light absorbing stains are dechromatized, more of the blue and green light from the argon laser is reflected. Therefore, as a second bleaching step, an infrared light generating laser may be used in conjunction with a free oxygen radical generating composition to further whiten teeth that have already been treated with an argon laser. In a preferred embodiment, a carbon dioxide ($CO_2$) laser is used. The infrared energy increases the temperature of the hydrogen peroxide, thus accelerating its decomposition into water and a free oxygen radical. The infrared energy is quickly absorbed by the hydrogen peroxide and water present on the surface of the tooth enamel during the bleaching process. In addition, the nonliving tooth enamel acts as a heat sink to protect the living parts of the teeth from the energy of the laser. Thus, for lightly stained teeth, such as in teeth stained with tanic acid, an infrared laser is more effective than an argon laser because the infrared energy interacts directly with the hydrogen peroxide.

A carbon dioxide laser is preferred for this step because it generates long wave infrared energy (10–11 micron wavelength), which is absorbed well by water. Thus, as the peroxide decomposes to water and a free oxygen radical, the water absorbs the infrared energy generated by the laser and is vaporized, thereby heat-activating any remaining peroxide. In order to avoid overheating the tooth pulp while using the carbon dioxide laser (i.e., raising the pulp temperature more than 6° C.), the maximum energy imparted to a tooth with a carbon dioxide laser should not exceed 15 joules. In a preferred embodiment, a total of 12.5 joules of energy is applied to each tooth during an application. This is achieved, e.g., by the use of a carbon dioxide laser with a 2.5 W power output for a period of 5 seconds per tooth. Higher and lower power outputs may be used, with the exposure time adjusted accordingly. In addition, the laser may be operated in pulsed mode or continuous wave. In a preferred embodiment, a carbon dioxide laser with a 3 mm spot beam is used. Once all teeth have been treated, any remaining bleaching mixture is removed from the teeth. If needed, the previous steps of applying the bleaching mixture and activating with the carbon dioxide laser may be repeated.

Although a $CO_2$ laser is preferred, other infrared lasers can be used. For example, an Neodymiun (Nd) Yttrium Arsenic Gallium (YAG) laser may also be used. However, Nd:YAG lasers have detrimental side effects due to the fact that they generate energy of a shorter wavelength than $CO_2$ lasers. The energy generated by an ND:YAG laser penetrates through tooth enamel more effectively than a $CO_2$ laser and is absorbed by the tooth pulp, resulting in a higher pulp temperature.

A catalyst and/or booster may also be used in conjunction with a $CO_2$ laser to further accelerate the bleaching process. One example of a booster is sodium perborate, which decomposes into peroxide to provide additional free oxygen radicals, thereby effectively increasing the concentration of the peroxide. Sodium perborate is preferable for use with the carbon dioxide laser, because its decomposition is accelerated by heat more so than light, as compared with the boosters that are used with the argon laser. Other compounds, such as sodium carbonate, sodium bicarbonate, calcium carbonate, ammonium hydroxide, sodium hydroxide, potassium hydroxide, and calcium hydroxide, act to raise the pH of the bleaching mixture so as to accelerate bleaching.

A preferred bleaching mixture for use with a $CO_2$ laser contains an oxygen radical generating agent such as a peroxide, a catalyst, a desensitizing and color stabilizing agent, a thickening agent, and a buffer for maintaining a desired pH range. The peroxide, the desensitizing and color stabilizing agent, the thickening agent, and the buffer and pH range may be the same as the first bleaching mixture. Typically, the catalyst or booster is used at a final concentration of 30%, although any concentration between 3% and 80% can be used. Once mixed, a 1 to 2 millimeter layer of the bleaching mixture is applied to the front surface of the patient's teeth.

Some of the foregoing catalysts, such as sodium carbonate and sodium bicarbonate, are also used as buffers. In addition to their pH raising effect, these compounds also act as catalysts due to their hydrophilic effect. In water, ions are surrounded by a layer of water molecules, called a primary hydration sphere. As the water molecules form this primary sphere surround the ions, their polarity is oriented to exert an enhanced hydrogen-bonding attraction on other water molecules. This results in formation of a secondary hydration layer around the first layer. Subsequent hydration layers can also form, depending on the size and charge of the ions. As water molecules are pulled into these hydration layers, the effective concentration of the oxygen radical generating agent is increased, resulting in greater instability and a faster rate of reaction.

For approximately 72 hours following the whitening of the teeth using the aforedescribed laser bleaching process, the teeth are generally more susceptible to staining because they are dehydrated. In order to prevent staining during this period and stabilize the color change, it is advantageous to provide patients with an in-home bleaching kit, comprising an 8–10% peroxide solution in a gel and either a custom made vacuum-formed mouth guard or disposable foam tray. Typically, the tray is worn for at least 15–30 minutes a day for 3–10 days following the laser bleaching procedure, depending on the patient.

It is to be understood that the method of the invention disclosed is a preferred embodiment thereof and that various changes and modifications may be made therein without departing from the spirit of the invention or scope as defined in the following claims.

I claim:

1. A method for whitening a patient's teeth comprising the steps of:
preparing a bleaching composition comprising an oxygen radical generating agent and a substance for raising the pH of said bleaching composition;
applying said composition to said teeth; and
exposing each of said teeth to laser light from an argon laser for a selected time interval to accelerate whitening.

2. A method as described in claim 1, wherein said oxygen radical generating agent is selected from the peroxide group consisting of hydrogen peroxide, carbamide peroxide, calcium carbonate peroxide, and sodium carbonate peroxide.

3. A method as described in claim 2, wherein said argon laser has a wavelength range in the visible spectrum between approximately 450 and 530 nanometers and each tooth to be treated is exposed to approximately 24 joules of energy from said argon laser.

4. A method as described in claim 1, wherein said pH-raising substance is sodium hydroxide.

5. A method as described in claim 1, wherein said pH-raising substance is potassium hydroxide.

6. A method as described in claim 1, wherein said pH-raising substance is calcium hydroxide.

7. A method as described in claim 1, wherein said pH-raising substance is ammonium hydroxide.

8. A method as described in claim 1, wherein said pH-raising substance is selected from the group consisting of sodium carbonate, sodium bicarbonate, and calcium carbonate.

9. A method as described in claim 1, wherein said composition further comprises:
a desensitizing and color stabilizing agent selected from the group consisting of fluoride, calcium, and phosphate and providing a concentration of said desensitizing and color stabilizing agent in said mixture between 0.1% and 10%.

10. A method as described in claim 1, wherein said argon laser has a wavelength range in the visible spectrum between approximately 450 and 530 nanometers and each tooth to be treated is exposed to approximately 24 joules of energy from said argon laser.

11. A method as in claim 1, wherein said bleaching composition further comprises a yellow pigment.

12. A method as described in claim 1, further comprising:
preparing a second bleaching composition comprising an oxygen radical generating agent;
applying said second composition to said isolated teeth; and
exposing said teeth to laser light from a carbon dioxide laser for a selected time interval to accelerate whitening.

13. A method as in claim 1 wherein said time interval is selected to provide a total of approximately 24 joules to each of said isolated teeth.

14. A method as in claim 1 wherein, prior to said exposing step, said composition is removed after a period of 15–60 minutes and replaced with additional composition.

15. A method as in claim 1 further comprising applying an 8–10% peroxide solution to said teeth for at least 15–30 minutes a day for a period of 3–10 days following said exposing step.

16. A method for whitening a patient's teeth comprising the steps of:
isolating the teeth to be treated;
preparing a bleaching composition comprising an oxygen radical generating agent and a substance for raising the pH of said bleaching composition;
applying said composition to said isolated teeth; and
exposing each of said isolated teeth to laser light for a selected time interval to accelerate whitening.

17. A method as described in claim 16, wherein said oxygen radical generating agent is selected from the peroxide group consisting of hydrogen peroxide, carbamide peroxide, calcium carbonate peroxide, and sodium carbonate peroxide.

18. A method as described in claim 16, wherein said pH-raising substance is sodium hydroxide.

19. A method as described in claim 16, wherein said pH-raising substance is potassium hydroxide.

20. A method as described in claim 16, wherein said pH-raising substance is calcium hydroxide.

21. A method as described in claim 16, wherein said pH-raising substance is ammonium hydroxide.

22. A method as described in claim 16, wherein said pH-raising substance is selected from the group consisting of sodium carbonate, sodium bicarbonate, and calcium carbonate.

23. A method as described in claim 16, wherein said laser is a carbon dioxide laser.

24. A method for whitening a patient's teeth comprising the steps of:

preparing a bleaching composition comprising a peroxide selected from the group consisting of hydrogen peroxide, carbamide peroxide, calcium carbonate peroxide, and sodium carbonate peroxide, and a substance for raising the pH of said bleaching composition to a pH between approximately 7 and 11;

applying said composition to said teeth; and exposing each of said teeth to laser light from an argon laser for a selected time interval to accelerate whitening.

25. A method as described in claim 24, wherein said pH-raising substance is sodium hydroxide.

26. A method as described in claim 24, wherein said pH-raising substance is potassium hydroxide.

27. A method as described in claim 24, wherein said pH-raising substance is calcium hydroxide.

28. A method as described in claim 24, wherein said pH-raising substance is ammonium hydroxide.

29. A method as described in claim 24, wherein said pH-raising substance is selected from the group consisting of sodium carbonate, sodium bicarbonate, and calcium carbonate.

* * * * *

UNITED STATES PATENT AND TRADEMARK OFFICE
CERTIFICATE OF CORRECTION

PATENT NO.   : 6,254,388 B1
DATED        : July 3, 2001
INVENTOR(S)  : Yarborough It is certified that error appears in the above-identified patent and that said Letters Patent is hereby corrected as shown below:

Column 1,
Line 65, now reads "35i%", should read -- 35% --.

Column 6,
Line 67, now reads "ND:YAG", should read -- Nd:YAG --.

Signed and Sealed this

Fifteenth Day of January, 2002

Attest:

Attesting Officer

JAMES E. ROGAN
Director of the United States Patent and Trademark Office